(12) United States Patent
Gogol, Jr. et al.

(10) Patent No.: US 6,482,649 B1
(45) Date of Patent: Nov. 19, 2002

(54) ACOUSTIC CONSUMPTION MONITOR

(75) Inventors: Carl A. Gogol, Jr., Manlius, NY (US); Abdul Wajid, East Syracuse, NY (US); Gary Rubloff, Ellicott City, MD (US)

(73) Assignee: Leybold, Inficon, Inc., East Syracuse, NY (US)

( * ) Notice: Subject to any disclaimer, the term of this patent is extended or adjusted under 35 U.S.C. 154(b) by 0 days.

(21) Appl. No.: 09/404,136

(22) Filed: Sep. 23, 1999

Related U.S. Application Data

(63) Continuation-in-part of application No. 08/902,419, filed on Jul. 29, 1997, now abandoned.

(51) Int. Cl.[7] .................. G01N 33/00; G01N 29/02
(52) U.S. Cl. .................. 436/34; 73/24.06; 427/8; 436/72; 436/76; 436/155; 436/181
(58) Field of Search .................. 436/34, 72, 76, 436/155, 181, 183; 73/24.06; 427/8

(56) References Cited

U.S. PATENT DOCUMENTS

| | | | |
|---|---|---|---|
| 3,449,071 A | * | 6/1969 | Campbell et al. |
| 3,919,968 A | | 11/1975 | Sandmann et al. |
| 4,148,931 A | | 4/1979 | Reuschel et al. |
| 4,381,894 A | | 5/1983 | Gogol, Jr. et al. |
| 4,388,342 A | | 6/1983 | Suzuki et al. |
| 4,681,640 A | | 7/1987 | Stanley |
| 4,857,136 A | | 8/1989 | Zajac |
| 5,032,435 A | | 7/1991 | Biefield et al. |
| 5,190,913 A | | 3/1993 | Higashiyama et al. |
| 5,392,635 A | | 2/1995 | Cadet et al. |
| 5,431,734 A | | 7/1995 | Chapple-Sokol et al. |
| 5,501,098 A | | 3/1996 | Cadet et al. |
| 5,525,156 A | | 6/1996 | Manada et al. |
| 5,528,924 A | | 6/1996 | Wajid et al. |
| 5,534,066 A | | 7/1996 | O'Neill et al. |
| 5,540,777 A | | 7/1996 | Barbee et al |
| 5,768,937 A | | 6/1998 | Wajid et al. . |

FOREIGN PATENT DOCUMENTS

| | | | |
|---|---|---|---|
| EP | 311446 | * | 12/1989 |
| JP | 8-222182 | | 8/1996 |

OTHER PUBLICATIONS

G.H. Fan et al., *J. Crystal Growth*, 1992, 124, 49–55.
N. Herlin et al., *J. Phys. Chem.*, 1992 96, 7063–7072.
B.A. Sacha et al., *Proc.–Inst. Environ. Sci.*, 1990 36th, 373–378.
G. Cadet et al., *Proc.–SPIE–Int. Soc. Opt. Eng.*, 1993, 1796, 298–309.
K. Hanaoka et al., *Jpn. J. Appl. Phys.*, 1993 32 part 1, 4774–4778.
L.L. Tedder et al., *J. Vac. Sci. Technol. A*, 1996, 14, 267–270.
M. Ganz et al., *J. Electrochem. Soc.*, 1996, 143, 1654–1661.
G. W. Rubloff et al., *Proc.–Electrochem. Socl*, 1996, 96–5, 163–170.
A. Wajid et al., *J. Cryst. Growth*, 1997 170, 237–241.
J. Musolf, *J. Alloys Compd.*, 1997 251, 292–296.
Tallman, *Acoustic Gas Analyzer*, Los Alamos Scientific Lab., Art. vol. 17, No. 1.
J. P. Stagg, *Reagent Concentration Measurements*, Stc. Tech. Ltd., UK, May 6, 1994.

* cited by examiner

*Primary Examiner*—Arlen Soderquist
(74) *Attorney, Agent, or Firm*—Wall Marjama & Bilinski LLP

(57) ABSTRACT

A method of determining the reaction efficiency of a CVD process reactor by which a reactive gas combination entering the reactor deposits a solid reaction product as a thin film onto a substrate. The composition of the reactive gas combination is measured by an acoustic cell which is disposed downstream from the outlet port of the reactor to determine the reactor's efficiency. Determination of the reactor's efficiency allows the growth rate of the thin film to be determined as well as associated rates of the products which have been exhausted from the reactor.

6 Claims, 5 Drawing Sheets

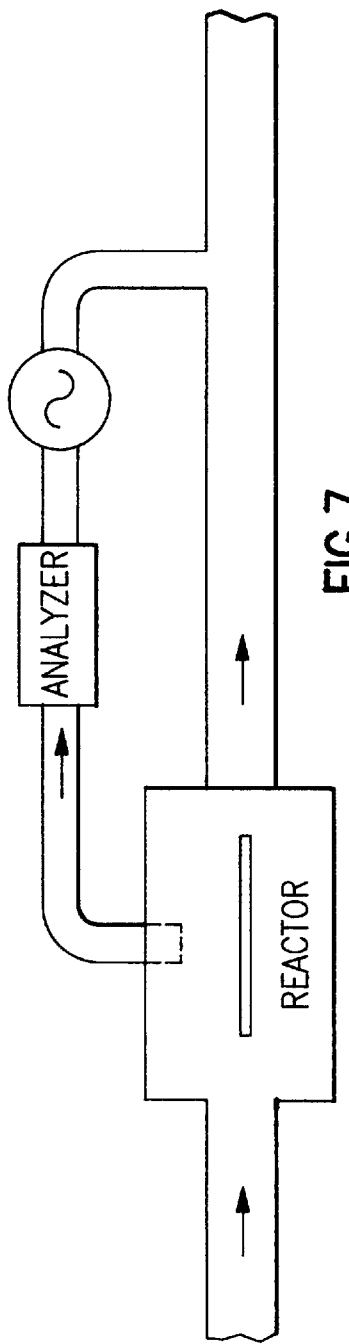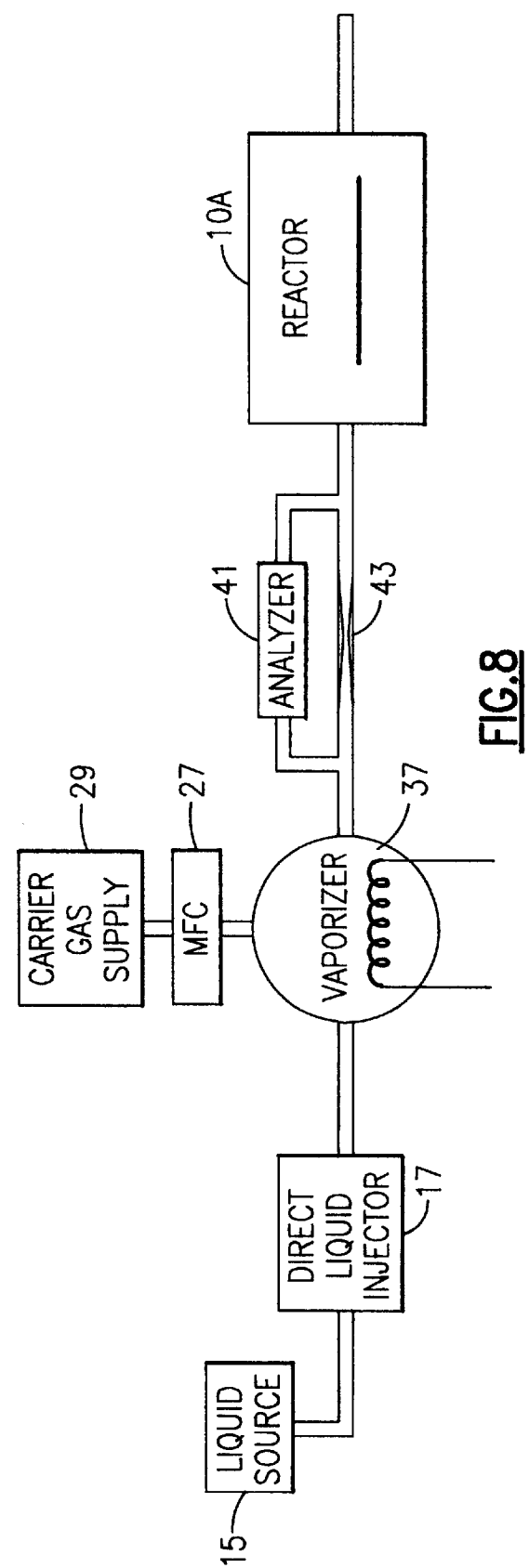

ACOUSTIC CONSUMPTION MONITOR

CROSS REFERENCE TO RELATED APPLICATIONS

This application is a continuation-in-part (CIP) application of U.S. patent application Ser. No. 08/902,419, filed on Jul. 29, 1997 now abandoned.

FIELD OF THE INVENTION

The invention relates to the field of substrate processing. More specifically, the invention relates to a method and related apparatus for continuously determining the reaction efficiency of a CVD (chemical vapor deposition) reactor. The reaction efficiency can be used to determine an in-situ growth rate of a metal organic or other material on a substrate, as well as provide quantitative information relating to reacted and unreacted components exhausted from the process reactor.

BACKGROUND OF THE INVENTION

The process of chemical vapor deposition (CVD) is extensively used to grow layers of various thicknesses of metals, semiconductors, dielectrics and the like. The CVD process typically requires that the desired growth materials be attached to a ligand or volatile adduct that allows the transport of the desired species in the gas phase to a reaction zone in a reactor where a substrate(s) is located. This complex molecule is referred to as the precursor. Different materials have different precursor structures.

Once in the reaction zone, a portion of the volatile precursor compound is decomposed, separating the volatile portion of the compound from the non-volatile portion, and leaving behind the desired solid deposit on the substrate. Typically, the decomposition reaction is driven thermally; that is, the substrate is heated to a sufficiently high temperature such that when the volatile compound contacts the substrate, sufficient energy is made available to break the connectivity between the volatile ligand and the desired atom. The desired atom remains deposited on the substrate, while the volatile portion of the precursor gas is then exhausted from the reactor through an exit port. While thermal energy is the most obvious means for performing the above deposition reaction, it should be noted that CVD explicitly includes processes assisted by other excitation means, including plasma discharge and photo-assisted means, among others, both in the reactor and by upstream excitation of the source gases before they enter the reactor.

The engineering design of CVD process reactors is based on: (1) the transport and even distribution of the volatile species over the entire area of the substrate and (2) the creation of an even temperature profile over the entire surface of the substrate. Should these two criteria be met, the desired material will grow at a predictable rate evenly over the substrate. With experience, the producer learns the proper settings of precursor flow, temperature, and time to produce the correct thickness of a desired film.

To date, however, there is no apparatus available to a producer to verify that each of the learned parameters of flow and temperature are correct. Therefore, the producer must verify that the thickness is correct through trial and error after a growth run is complete and the substrate(s) have been removed from the reactor.

In addition, no means currently exists for determining a process reactor's utilization efficiency; that is, to determine how much of the precursor gas is consumed. This particular metric is increasingly important for controlling the cost of consumables. Utilization efficiency is also important to the environmentally conscious in order to understand information about the products which are exhausted from the CVD reactor.

SUMMARY OF THE INVENTION

A primary object of the present invention is to determine the exhausted reacted and unreacted by-products of any CVD reaction process.

Another primary object of the present invention is to improve the efficiency of chemical vapor deposition (CVD) process reactors.

Another primary object of the present invention is to quantitatively deduce the efficiency of a CVD reaction without relying on empirical data.

It is still another primary object of the present invention to be able to determine an in-situ growth rate and thickness of the thin film onto a substrate in a CVD reactor.

An example is described for oxygen and TEOS yielding silicon dioxide in a plasma enhanced CVD reactor (PECVD) per the following:

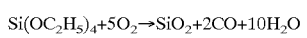

in which $SiO_2$ is the solid product. The reaction inputs will generally have excess oxygen; that is, greater than stoichiometric, to facilitate the growth of high quality material in a plasma process. Therefore, the exhaust stream will have:

in which w, $x_1$, y, and z are related to the mass quantities of gases in the exhaust stream. The quantities of CO and $H_2O$ are related in the ratio of 1:5 because they predominantly result from the disassociation reaction, the abundance of these species resulting from wall desorption or outgassing being insignificant.

The present invention can also be applied to thermal CVD processes conventionally carried out in hotwall quartz furnace tubes including, but not limited to, the following conventionally standard manufacturing processes:

oxide from TEOS at low pressure; PSG, BSG, BPSG, i.e.: TEOS oxide with boron and/or phosphorous doping; silane-based oxide (using $SiH_4$ or higher silanes, with $O_2$ or $N_2O$); silane-based nitride (using $SiH_4$ or higher silanes, with $NH_3$); polysilicon or silicon epitaxy from $SiH_4$, $Si_2 2H_6$, or other silanes, or from Cl-containing silicon precursors (e.g.: $SiCl_4$, $SiClH_3$, etc.).

According to yet another preferred aspect of the invention, there is provided an apparatus for determining the reaction efficiency of a CVD reactor, said reactor having a defined cavity for retaining at least one substrate onto which is deposited a solid reaction product from a reacted binary gas mixture (aA+bB⇌cC+dD), said reactor further including an inlet port and an outlet port, said apparatus comprising:

means for determining the composition of said gas mixture at the outlet port of the reactor;

means for determining the composition of said gas mixture at the inlet port of the reactor;

wherein said outlet composition determining means is an acoustic cell capable of measuring relative differences in the speed of sound for gases passing therethrough, in which the reacted product is derived from the relation:

$$\left(\frac{\overline{c}_o}{\overline{c}}\right)^2 = \frac{(1-\Delta)M_A + \left(x - \frac{b}{a}\Delta\right)M_B + c\frac{\Delta}{a}M_C}{M_A + xM_B}.$$

$$\left[\frac{1+x}{1+x+\frac{\Delta}{a}(c-b-a)}\right]^2 \left[\frac{\frac{1-\Delta}{\gamma_A} + \frac{x-\frac{b}{a}\Delta}{\gamma_B} + c\frac{\Delta}{\gamma_C}}{(1/\gamma_A + x/\gamma_B)}\right]$$

in which:

$\Delta$=reacted product(reacted fraction of species A);

$M_A$, $M_A$, $M_C$=molecular weights of species A, B, C;

$Y_A$, $Y_B$, $Y_C$=specific heat ratios of A, B, C;

x=mole fraction of A in B; and $$\left(\frac{\overline{c}_o}{\overline{c}}\right)$$

is the frequency ratio of the gas mixture between a reacted mode and a bypass mode.

According to a preferred embodiment, a pair of acoustic cells are used to determine gas compositions at the inlet and outlet sides of the reactor, respectively.

As is known, an acoustic cell can be used to determine the composition of a binary gas mixture from knowledge of the molecular weights of the gases in a particular gas mixture, their individual specific heat ratios ($C_p/C_v$) and the measurement of the speed of sound. A more complete description of an acoustic cell used in conjunction with chemical vapor deposition processes can be found in commonly owned U.S. Pat. No. 5,768,937, the entire contents of which are hereby incorporated by reference.

According to this invention, and by calculating the consumption of precursor gas within the reactor based on a specific chemistry; (e.g., the reaction efficiency), a number of benefits can be derived. First, the growth rate of thin film material can be determined from quantitative information derived from the pair of acoustic cells, disposed at the inlet and the outlet of the reactor, and a knowledge of the reaction chemistry or some other independent empirical determination of the absolute efficiency of the acoustic cell measurement.

Second, by understanding the reaction efficiency, and by use of the acoustic cells which are capable of determining gas composition data at the outlet side of the reactor, information relating to the exhausted gas composition can be derived. Knowledge of the species and quantity of emission gases allows determination of this "efficiency" parameter, which is becoming increasingly important from an environmental standpoint stemming from growing awareness of producers, as well as promulgated standards implemented by groups such as the Environmental Protection Agency, among others.

According to a preferred embodiment of the invention, a frequency ratio related to the speed of sound ($c/c_o$) is measured at the outlet side of the reactor by a first acoustic cell while a second acoustic cell measures the composition of the binary gas combination at the inlet; that is, an arriving composition ratio at the reactor inlet. According to the present method, a derivation of the reaction fraction ($\Delta$) can then be calculated from this data alone for each reaction process. The above information provides the reactor's efficiency. Using the derived information for the quantity of the reacted product, along with independent knowledge of the inlet's total molar flow rate, the total area of the substrate, and other known information related to the structure of the resulting thin film, the growth rate of the thin film can then also be derived.

In addition to deriving the thin film's growth rate, information pertaining to the reacted and unreacted products exhausted from the reactor can also be derived using the reaction efficiency, as well as known information pertaining to the mass flow entering the reactor chamber and the dominant chemical reaction in a manner described in greater detail below.

Alternately, the above information could also be obtained using a single acoustic cell at the outlet side of the reactor and by either reducing the temperature or otherwise turning off the reaction, or by adding a by-pass line.

An advantage of the present invention is that the thin film growth rate onto a substrate resulting from a chemical vapor deposition (CVD) reaction can be calculated easily and quickly using known data and at least one acoustic cell capable of determining the composition of the gas mixture.

Another advantage of the present invention is that a quantitative analysis of the reaction at the inlet and outlet sides of the reactor is useful in calculating the reaction efficiency and thereby determining information relating to the exhaust product, including the presence of unreacted gases resulting from an uncompleted reaction.

These and other objects, features, and advantages will now be described in the following Detailed Description which should be read in conjunction with the accompanying drawings.

BRIEF DESCRIPTION OF THE DRAWINGS

FIG. 7 is a schematic view of an internal sampling method from the reactor; and

FIG. 8 is a partial schematic view of an alternate precursor-carrier gas introduction to a reactor.

DETAILED DESCRIPTION

The following description relates to a particular preferred embodiment utilizing a specific chemical vapor deposition (CVD) reactor and a known reaction chemistry. It will be readily apparent that other alternate embodiments using the concepts described herein can be easily imagined by one of ordinary skill in the field.

Figure 1:
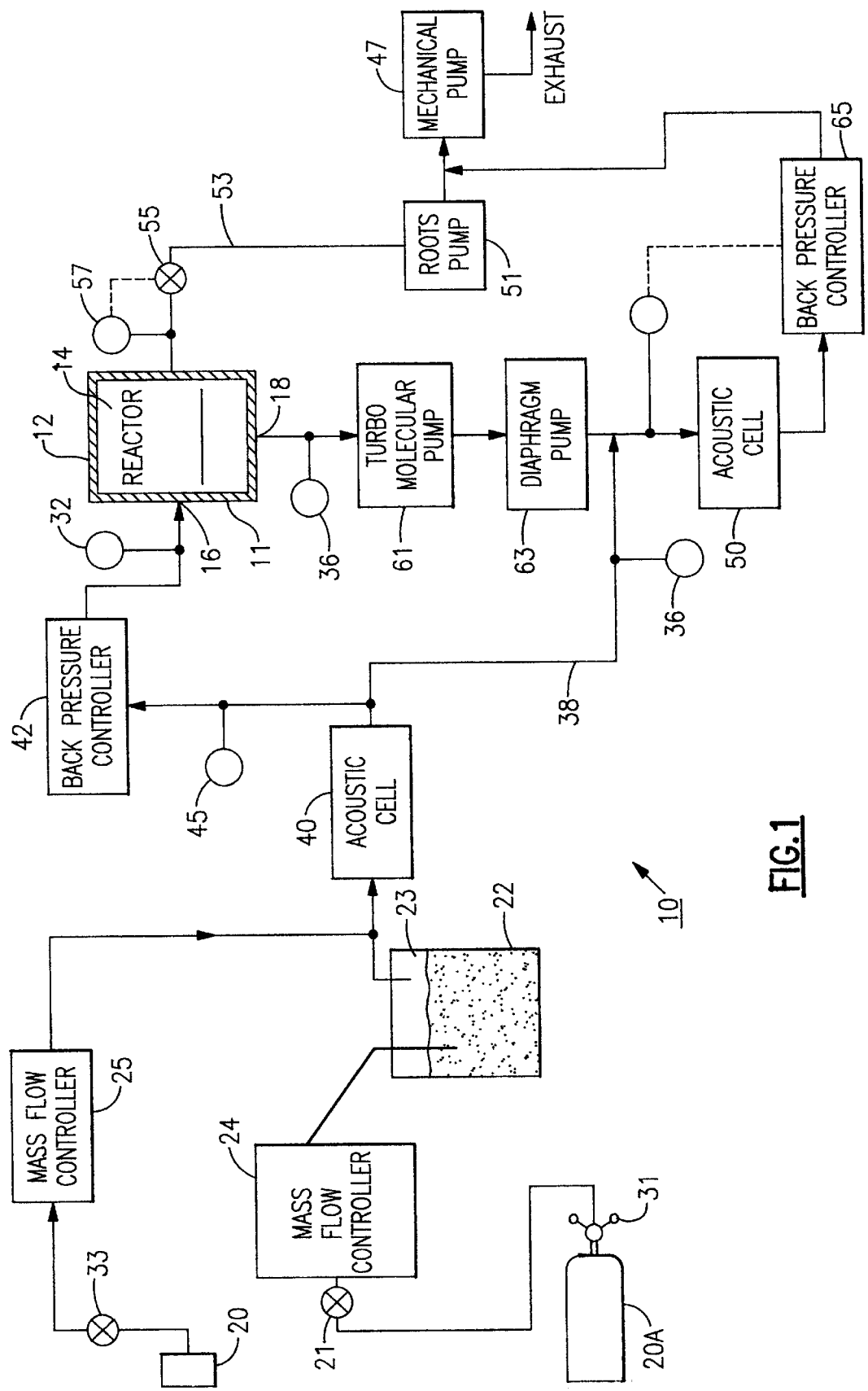
FIG. 1 is a diagrammatic view of a CVD reactor system having measurement apparatus arranged according to a specific embodiment of the present invention.

Referring to FIG. 1, there is shown a diagrammatic view of a CVD reactor system 10 in accordance with a preferred embodiment of the present invention. The system 10 includes a CVD reactor 11 having a housing 12 with a defined internal cavity or chamber 14 and respective inlet and outlet ports 16, 18 (shown only schematically in FIG. 1).

According to this embodiment, a carrier gas bottle 20 is interconnected to a bubble chamber 22 containing high purity liquid or solid as a CVD precursor. The bubble chamber 22 is designed to allow carrier gas flow through the precursor while some small amount of the precursor is evaporated into the carrier gas. The flow of the carrier gas ($H_2$ according to this embodiment) into the bubble chamber 22 is controlled by a first mass flow controller or flow meter 24 and associated regulating valve 21 at a fixed rate and pressure by known means.

The precursor is picked up from the liquid and leaves the bubble chamber 22 in gaseous form with the carrier gas obtained from the headspace 23. A dilution flow of gas from a container 20A can be selectively carried in a parallel circuit by opening an adjacent regulating valve 33 into a second mass flow controller 25 leading to that leaving the headspace 23.

Figure 4:
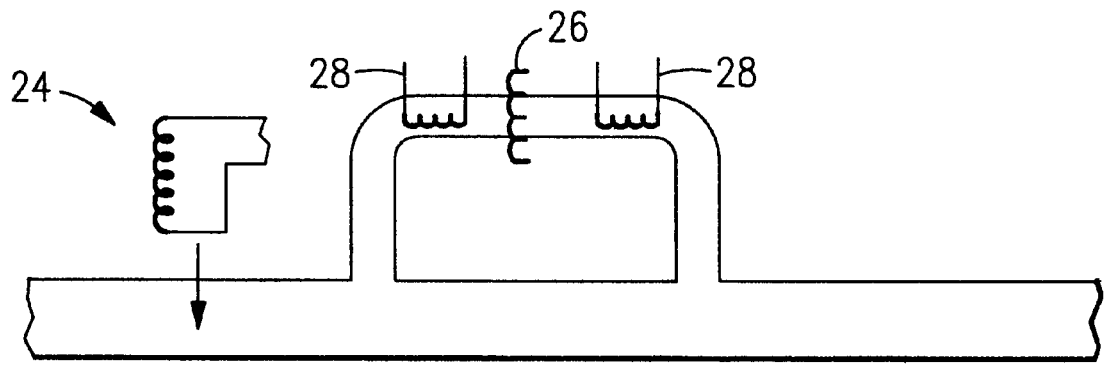
FIG. 4 is a pictorial diagram of a mass flow controller used in the apparatus of FIG. 1.

As shown in FIG. 4, and according to the present embodiment, each of the mass flow controllers 24, 25 include a pair of fine platinum resistance thermometers 28 spaced an equal distance from a small heater element 26. The output from the resistance thermometers 28 control an adjacent solenoid-controlled leak valve 35, in a manner commonly known to those in the field.

Alternatively, and referring briefly to FIG. 8, some CVD processes utilize direct conversion of the precursor from the liquid state to the vapor state by the careful quantitative metering of the liquid precursor from a source 15, such as using a liquid injector 17 and its subsequent vaporization by a vaporizer 37. This vapor is usually carried to the reactor 14 by a carrier gas, such as hydrogen, oxygen, ammo ($NH_3$) or argon added to the vaporizer 37 from a supply 29, as monitored by an in line mass flow controller 27.

One example of large commercial interest is oxygen ($O_2$) and TEOS. It is consequently important to know the composition ratio of this mixture as it is carried to the reactor. Again, it is possible to pass all of the mixture through the analyzing means, but in many cases, it will be necessary to draw only a representative sample through the analyzer 41 because of flow limitations through the sensor. The flow restriction, shown as 43, is used to ensure some portion passes through the acoustic cell. In these cases, a bypass mode of operation will be necessary and can be implemented as described in greater detail below, according to FIG. 5, 6 or 7 as circumstances dictate.

Referring back to FIG. 1, a first acoustic gas composition cell 40 is positioned adjacent the inlet port 16 external to the reactor 10 (i.e., upstream), while a second acoustic gas composition cell 50 is positioned substantially downstream of the outlet port 18. A by-pass line 38 interconnects the first and second acoustic cells 40, 50, but effectively bypasses the reactor 10. Though, the acoustic cells 40, 50 described by this embodiment are essentially identical, this limitation is not absolutely critical to the workings of the present invention; that is, the acoustic cells may vary in size and configuration. A back pressure controller 42 having an external pressure gauge 45 is used for maintaining a constant pressure in the bubble chamber 22 and thereby aiding the stability of precursor pickup by the carrier gas.

Within the cavity 14 of the reactor 10 is a substrate 30 typically made from silicon or other materials, such as GaAs, or even various metals or glasses. The reactor 10 also includes means (not shown) for uniformly heating the substrate 30 to a reacting temperature. The specific workings and operational details of the process reactor 10 are known and do not form an essential part of the present invention, therefore no further discussion is required except as needed.

Valves 32, 34, and 36 control the flow of the gas mixture into and out of the reactor cavity 14, and the by-pass line 38, respectively. In addition, a Roots pump 51, such as generally described at page 7.5 of the *Product and Technology Reference* (1994) published by Leybold Inficon, Inc., the contents of which are herein incorporated by reference, is interconnected through an exhaust line 53 via a throttling valve 55, the line being used to maintain reactor pressure using a feedback gauge 57. An exhaust pump 47 or other means, such as a blower, guides the exhausted materials from the second acoustic gas composition cell 50 to atmosphere.

Often, for example, exhaust gases are routed through "scrubbers" (not shown) to break down complex organic molecules to harmless simple ones. In order to boost the pressure to allow fluency of the acoustic cell 50, a turbomolecular pump 61 and a diaphragm pump 63 are disposed between the outlet port 18 of the reactor 10 and the second acoustic cell 50. Alternately, a multistage piston pump (not shown) or other suitable means of boosting the pressure to approximately −50 torr as required for the operation of the acoustic cell 50 can be utilized. A back pressure controller 65 buffers the second acoustic gas composition cell from wide pressure swings with the output from the second acoustic cell 50 leading to the exhaust pump 47.

Figure 2:
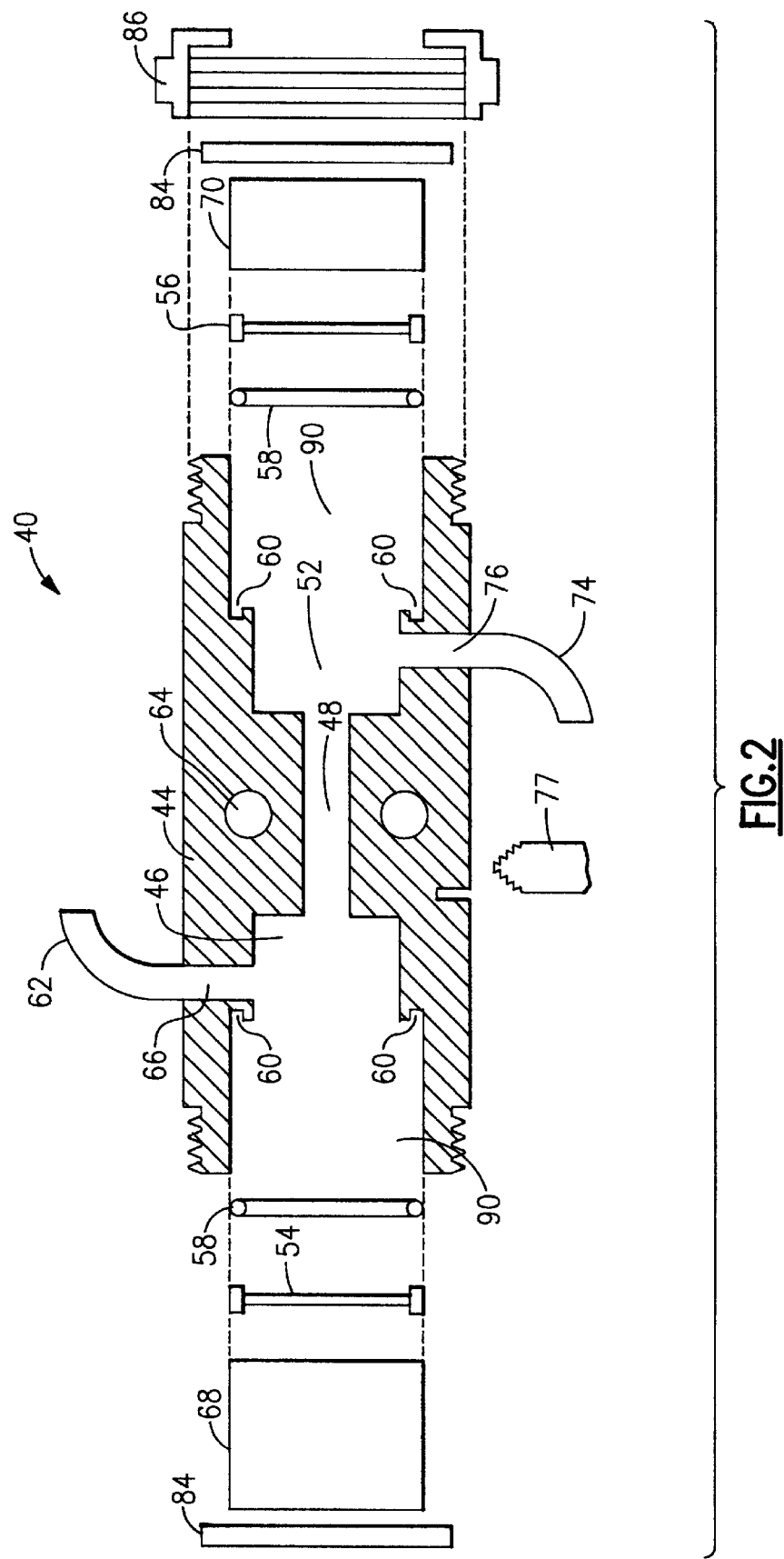
FIG. 2 is a pictorial cross-sectional view of an acoustic cell used in accordance with the reactor system illustrated in FIG. 1.

Referring to the exploded FIG. 2, further details are herein provided concerning the first and second acoustic gas composition cells 40, 50. For the sake of convenience, only the first acoustic cell 40 is detailed with the second cell 50 having similar features. The acoustic cell 40 includes a housing 44, preferably made of a metallic material and including a plurality of acoustic cavities 46, 48, and 52 which define a resonator chamber 64. First and second diaphragms 54, 56, each preferably made from a non-oxidizing and non-reacting metal alloy, such as Inconel, are installed in the housing 44 using a sealing O-ring 58 which is fit into an annular groove 60. The annular groove 60 is designed to make a leak tight seal when a corresponding diaphragm 54, 56 is sufficiently pressed into it to provide intimate sealing contact with the front surface of the groove. A gas inlet tube 62 is connected to the acoustic cavity 46 via a gas inlet 66, while a corresponding gas outlet tube 74 is connected to the acoustic cavity 52 via gas outlet 76. A pair of heater mounting holes 64 are preferably drilled through the housing 44 to maintain the cells 40, 50 at a given temperature within about 0.1° C. or less of the set point as measured by a platinum resistance thermometer 77. In use, a driving means, such as a driving microphone 68, at one end of the cell housing 44 sends an acoustic signal through the gas flowing through the cell housing 44 which is received by a receiving microphone 70 or other receiving means at the other end of the cell housing. The microphones 68, 70 are inserted into a chamber 90 provided on either side of the housing 44. End washers 84 retain each microphone 68,70, along with an additional housing 86, (only one side shown) and provide sufficient force to compress the O-ring 58.

It is also possible to directly excite the driving diaphragm 68 by electrostatic coupling means (not shown) or the direct application of a piezoelectric material (not shown) on the diaphragm. It is also possible to detect the motion of the receiving diaphragm 70 directly by capacitive displacement measurements or by using piezoelectric film material (not shown) directly applied to the diaphragm 68 to induce electrical signals which can be measured. Further details relating to the design of the present acoustic cell are found in previously incorporated U.S. Pat. No. 5,768,937.

In operation, the gas is flowed through the first acoustic gas composition cell 40 and a driving acoustic signal is transmitted through the gas where the signal is received on the other end. The acoustic signal is converted into an electrical signal which is subsequently processed by circuitry (not shown) to detect a resonant frequency resulting from the specific gases and their composition ratios. Based on this resonant frequency and the resonant frequency of the pure carrier gas, the composition of the binary gas mixture can be calculated. Additional details regarding the operation of the acoustic cells 40, 50 are provided in the above cross-referenced '937 patent.

Additional technical background is herein provided for purposes of understanding the present invention. According to the invention, an analysis of the composition of a gas is achieved by the measurement of the speed of sound in a specific gas media using the first and second acoustic gas composition cells 40, 50 in the manner briefly described above. For ideal gases and dilute mixtures of non-ideal gases in ideal gases, such as used in the CVD reactor 10, for a mixture of gases the speed of sound $\bar{c}$ is given by the equation:

$$\bar{c}^2 = \bar{\gamma}\frac{RT}{\bar{M}} \quad (1)$$

in which: $\bar{\gamma}$ is the average specific heat ratio of the gas mixture, $\bar{M}$ is the average molecular weight of the gas mixture, R is equal to 8311.7 mks units (commonly referred to as the Universal Gas Constant), and T is the temperature as measured in degrees Kelvin.

If the mole fraction of the precursor gas contained in a carrier gas is x, then the average specific heat ratio $\bar{\gamma}$ is written as the weighted harmonic average:

$$\frac{1}{\bar{\gamma}-1} = \frac{x}{\gamma_1 - 1} + \frac{1-x}{\gamma_2 - 1} \quad (2)$$

which can be rewritten as:

$$\bar{\gamma} = 1 + \frac{(\gamma_1 - 1)(\gamma_2 - 1)}{x(\gamma_2 - 1) + (1-x)(\gamma_1 - 1)} \quad (3)$$

The average molecular weight, $\bar{M}$, is the simple weighted average:

$$\bar{M} = xM_1 + (1-x)M_2 \quad (4)$$

in which the subscripts 1 and 2 denote the precursor gas and the carrier gas, respectively. The mole fraction information for a given binary gas combination is obtained from equations (1) through (4) as follows. For convenience, the following quantities are defined:

$$m = \frac{M_1}{M_2}; \quad (5)$$

$$g = \frac{\gamma_1}{\gamma_2}; \text{ and} \quad (6)$$

$$h = \frac{1}{\gamma_2}. \quad (7)$$

Substituting the values of equations (5)–(7) into equations (1)–(4):

$$\bar{M} = M_2((m-1)x + 1) \quad (8)$$

$$c^2 = c_2^2 h + \frac{\frac{(g-h)(1-h)}{x(1-g)+(g-h)}}{1+(m-1)x} \quad (9)$$

From equation (1), we obtain:

$$c_2 = \sqrt{\frac{\gamma_2 RT}{M_2}}. \quad (10)$$

In addition, and for a binary combination of gases:

if $n_1$=number of moles of gas A and $n_2$=number of moles of gas B entering the system, and:

x=mole ratio or mole fraction of source gas such that:

$$x = n_2/n_1 \quad (11)$$

In general, it is known that a chemical reaction of the form:

$$aA + bB \leftrightarrows cC + dD \quad (12)$$

may then be rewritten as:

$$n_1 A + n_2 B \rightarrow \left\{ n_1 \Delta A + \left(\frac{b}{a}n_1\Delta\right)B \right\} + n_1(1-\Delta)A + \left(n_2 - \frac{b}{a}n_1\Delta\right)B \quad (13)$$

where $\Delta$=fraction of component A which undergoes reaction.

Rewriting the above relation:

$$n_1 A + n_2 B \rightarrow \frac{n_1\Delta}{a}\{aA + bB\} + (1-\Delta)n_1 A + \left(n_2 - \frac{b}{a}n_1\Delta\right)B \quad (14)$$

or $$\rightarrow \left[\frac{n_1\Delta}{a} \cdot dD\right] + \frac{n_1\Delta}{a}cC + (1-\Delta)n_1 A + \left(n_2 - \frac{b}{a}n_1\Delta\right)B \quad (15)$$

in which:

$$\left[\frac{n_1\Delta}{a} \cdot dD\right]$$

is the solid portion that would not be available in the gas phase for analysis.

The gas composition after reaction is therefore:

$$\frac{n_1\Delta}{a}cC + (1-\Delta)n_1 A + \left(n_2 - \frac{b}{a}n_1\Delta\right)B \quad (16)$$

having three components A, B, C in the proportions of $$n_1(1-\Delta), n_1(x - b/a\Delta), \text{ and } n_1\frac{c}{a}\Delta, \text{ respectively.}$$

The important gas-related parameters are found as:

a) Molecular weight $\overline{M} =$ (17)

$$\left[\frac{n_1(1-\Delta)M_A + n_1\left(x - \frac{b}{a}\Delta\right)M_B + \frac{n_1 c \Delta M_C}{a}}{S}\right]$$

where $$S = n_1(1-\Delta) + n_1\left(x - \frac{b}{a}\Delta\right) + n_1\frac{c}{a}\Delta \quad (18)$$

rewriting $$S = n_1\left[(1+x) + \frac{\Delta}{a}(c - b - a)\right] \quad (19)$$

b) The specific heat ratio $\overline{\gamma}$ is obtained from the following:

$$\frac{S}{\overline{\gamma}} = \frac{n_1(1-\Delta)}{\gamma_A} + \frac{n_1\left(x - \frac{b}{a}\Delta\right)}{\gamma_B} + \frac{n_1 c \Delta / a}{\gamma_C} \quad (20)$$

Where $\gamma_A, \gamma_B, \gamma_C$ respectively represent specific heat ratios for the gas species A, B, and C.

Because we know the speed of sound c is given by equation (1):

$$\overline{c}^2 = \frac{\overline{\gamma} RT}{\overline{M}} \quad (21)$$

rewriting $$\frac{RT}{\overline{c}^2} = \frac{\overline{M}}{\overline{\gamma}} \quad (22)$$

Therefore:

$$\frac{RT}{\overline{c}^2} = \frac{n_1(1-\Delta)M_A + n_1\left(x - \frac{b}{a}\Delta\right)M_B + \frac{n_1 c\Delta}{a}M_C}{S^2} \quad (23)$$

$$\left[\frac{n_1(1-\Delta)}{\gamma_A} + \frac{n_1\left(x - \frac{b}{a}\Delta\right)}{\gamma_B} + \frac{n_1 c\Delta/a}{\gamma_C}\right]$$

which equals:

$$\frac{(1-\Delta)M_A + \left(x - \frac{b}{a}\Delta\right)M_B + \frac{c\Delta}{a}M_C}{\left[1 + x + \frac{\Delta}{a}(c - b - a)\right]^2} \cdot \left[\frac{1-\Delta}{\gamma_A} + \frac{x - b\Delta/a}{\gamma_B} + \frac{c\Delta/a}{\gamma_c}\right] \quad (24)$$

Figure 5:
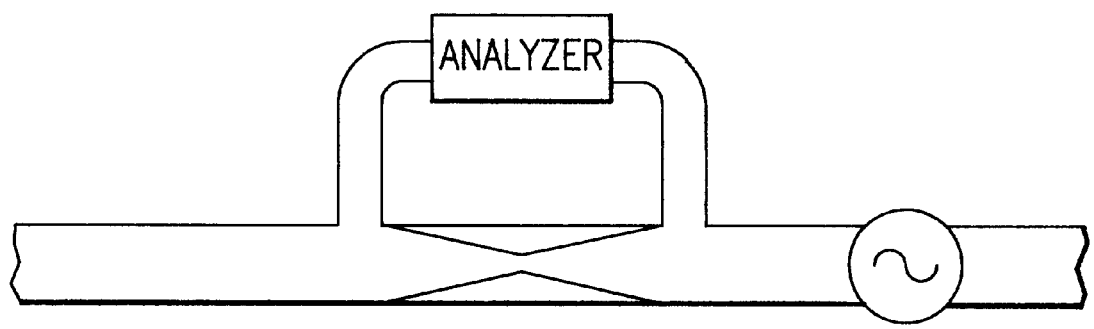
FIGS. 5 and 6 are alternate schematic views of by-pass gas flow.
Figure 6:
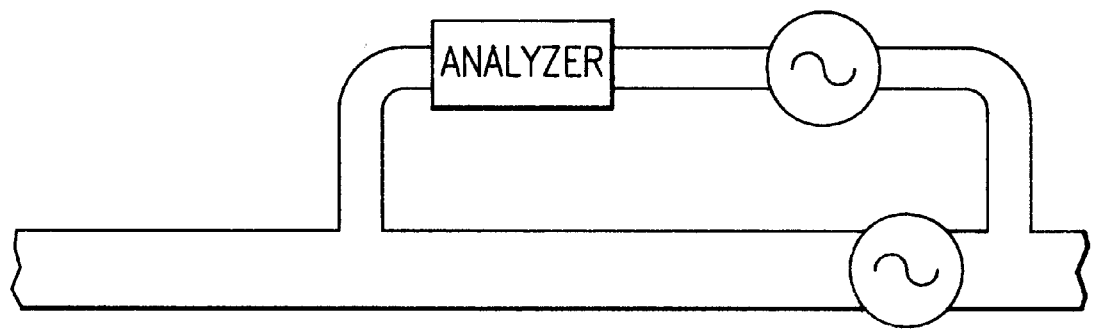

Many means of instrumental analysis are not capable of analyzing all of the gases flowing into a reactor 10. In this case, the gas flow is split, with only part of the gas flow being through the instrument. This bypass mode of operation, or this splitting of the gas flows, will be accomplished by either the natural flow division that comes from impedance ratios of the measurement instrument's flow to the main flow channel, as shown in FIG. 5, or by the flow induced through an instrument by a pump means; see FIG. 6.

In either case, it is important to insure that the sample is represented of the total flow to or from the reactor 10. In some special cases, it might be appropriate to draw a sample from a specific position within the reactor as shown in FIG. 7.

In the described bypass mode, no reaction takes place so the inlet's composition equals the outlet's composition and the average molecular weight for this special case is $\overline{M}_o$ given as:

$$\overline{M}_o = (n_1 M_A + n_2 M_B)/(n_1 + n_2) = \frac{M_A + xM_B}{1 + x} \quad (25)$$

and the specific heat ratio $\gamma_o$ for this special case is:

$$\frac{1+x}{\overline{\gamma}_o} = \frac{1}{\gamma_A} + \frac{x}{\gamma_B} \quad (26)$$

Therefore:

$$\frac{RT}{\overline{c}_o^2} = \frac{\overline{M}_o}{\overline{\gamma}_o} = \frac{M_A + xM_B}{(1+x)^2} \cdot \left[\frac{1}{\gamma_A} + \frac{x}{\gamma_B}\right] \quad (27)$$

Combining the ratio of speeds of sound between the bypass mode and the reaction mode produces the following equation:

$$\left(\frac{\overline{c}_o}{\overline{c}}\right)^2 = \frac{(1-\Delta)M_A + \left(x - \frac{b}{a}\Delta\right)M_B + c\frac{\Delta}{a}M_C}{M_A + xM_B} \cdot \quad (28)$$

$$\left(\left[\frac{1+x}{1 + x + \frac{\Delta}{a}(c-b-a)}\right]\right)^2 \left[\frac{\frac{1-\Delta}{\gamma_A} + \frac{x - \frac{b}{a}\Delta}{\gamma_B} + c\frac{\Delta}{\gamma_C}}{(1/\gamma_A + x/\gamma_B)}\right]$$

Therefore, and according to the above relationship, the frequency ratio at the outlet port 16 of the reactor 10 can be determined for a given reaction and inlet mole fraction. For purposes of the present invention, the decomposition reaction for tungsten hexafluoride and hydrogen having the below reaction equation is herein provided as a working example:

$$WF_6 + 3H_2 \rightarrow W + 6HF \quad (29)$$

The following parameters are known for each of the reaction components:

$M_A$=molecular weight of $WF_6$=297

$M_B$=molecular weight of $H_2$=2

$M_C$=molecular weight of $H_F$=20 a=1 b=3 c=6

$\gamma_A$=specific heat ratio of $WF_6$=1.16

$\gamma_B$=specific heat ratio of $H_2$=1.41

$\gamma_C$=specific heat ratio of HF=1.41

Figure 3:
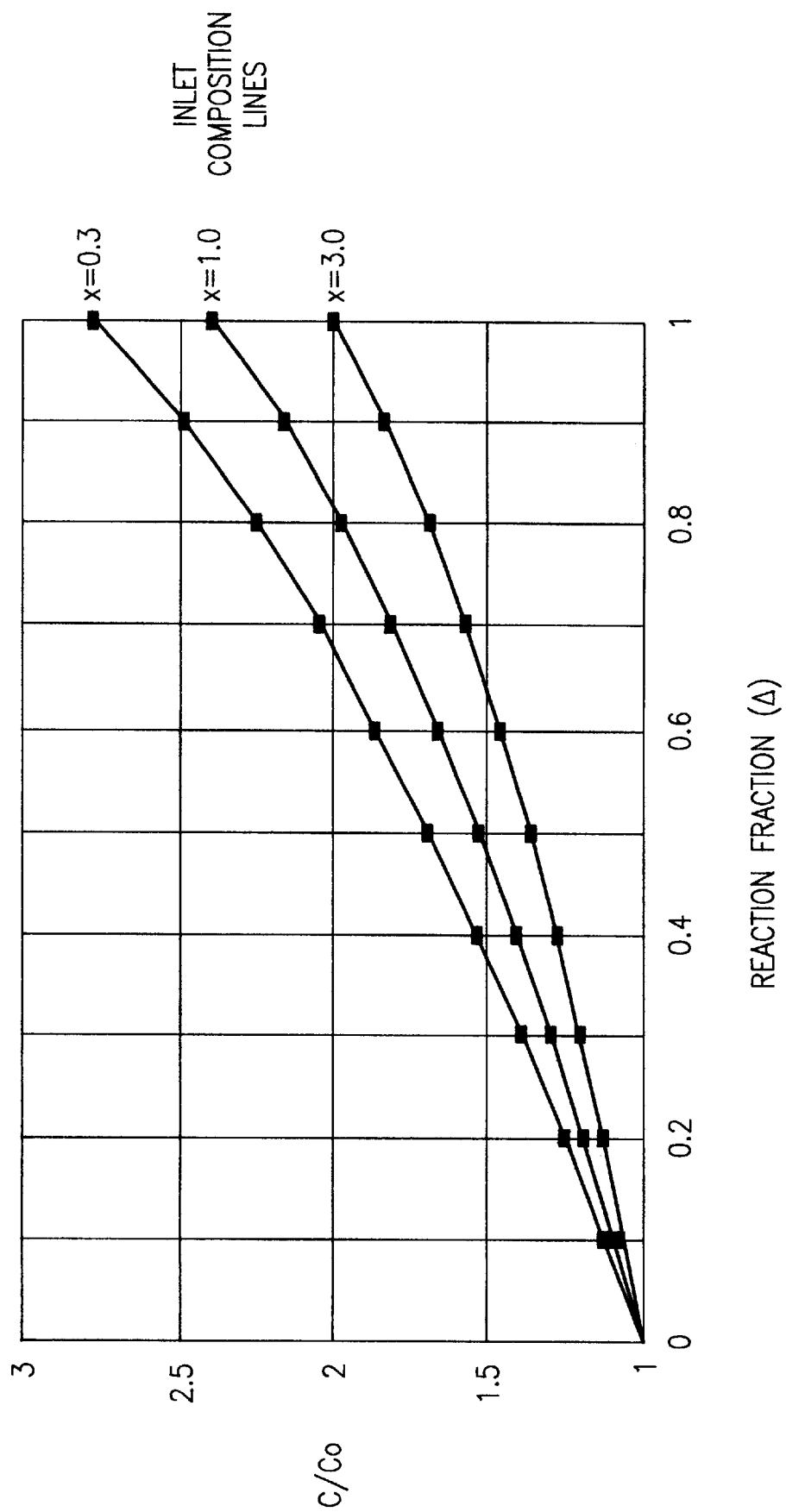
FIG. 3 is a graphical representation of a nomograph created for a specific binary gas mixture used in accordance with the system of FIGS. 1–2.

Therefore, substituting each of the above values into equation (28) above yields:

$$\left(\frac{\overline{c}_o}{\overline{c}}\right)^2 = \quad (30)$$

$$\left(\left[\frac{1+x}{1+x+2\Delta}\right]\right)^2 + \left[\frac{(1-\Delta)297 + (x - 3\Delta)2 + 6\Delta 20}{297 + 2x}\right]\left[1 - \frac{\Delta}{1.16} + \right.$$

$$\frac{x-3\Delta}{1.41} + \frac{\frac{6\Delta}{1.41}}{1/1.16 + x/1.41}$$

thereby producing the graphical representation or nomograph shown in FIG. 3.

Using the graphical information presented by FIG. 3, and according to this preferred embodiment, the reaction fraction ($\Delta$) can be derived using the first and second acoustic cells 40, 50.

First, the inlet composition (x) of the binary gas composition is measured and/or controlled by the first acoustic gas composition cell 40 using the associated mass flow meter 25 in a known manner.

As is known, a graphical representation can be made between the mole fraction (x) and sensor frequency ratio (speed of sound ratio) for a given binary gas composition using an acoustic cell. Using the second acoustic cell 50, the frequency ratio, $\bar{c}_o/\bar{c}$, can therefore be determined by measuring the speed of sound in the bypass mode using the bypass line 38, and the speed of sound for the reacted gas combination exhausted through the outlet port 18 of the reactor using valves 32, 34, 36. The reacted fraction ($\Delta$) is then calculated from equation (28) or can be deduced from the graphical representation of FIG. 3.

The reacted fraction ($\Delta$) provides the reaction efficiency of the process reactor 10. Subsequently, the total number of atoms deposited over time in the reactor 10 can be determined by the following equation:

$$G = F[6.02 \times 10^{23}/22.7 \text{ liters}][1 \text{ liter}/1000 \text{ std cc}]\Delta \tag{31}$$

where

G=total number of atoms deposited over unit time; e.g. (# atoms/min)

F=the measured flow rate of precursor into the reactor inlet (std cc/min);

$6.02 \times 10^{23}$ is Avogadro's number; and 22.7 liters is the molar gas volume at standard temperature and pressure;

$\Delta$=reacted fraction of precursor.

In general, the mass flow rate (F) of precursor is derived from and/or measured by the input's mass flow controller 25 and the inlet's measured (or controlled) mole fraction, x, using the acoustic cell 40.

$$F = wx(1 \text{ mole}/22.7 \text{ liters})(1 \text{ liter}/1000 \text{ stdcc}) \tag{32}$$

in which:

w=measured flow rate of input precursor (sccm); and x=mole fraction of precursor in the inlet.

Once the total number of atoms deposited over time, G, is known, then, a volumetric growth rate can be calculated as follows:

$$V = G \cdot \{a^3 \text{Å}^3/n\}\{10^{-24} \text{ cm}^3/\text{Å}^3\} \tag{33}$$

in which:

V=volumetric growth rate (cm³/min)

a=lattice parameter (angstroms, Å=$10^{-8}$ cm)

n=number of atoms in a unit cell.

The coefficients for a and n are commonly available from standard tables, such as found in a CRC Handbook of Chemistry and Physics or similar reference source. By knowing the substrate area, the volumetric growth rate (V) can be recalculated as the rate of thickness increase of the substrate(s):

$$R = V/A \tag{34}$$

in which

R=the rate of substrate thickness increase (Å/min); and

A=substrate area (cm²)

A key assumption of the above relationship is that the only surfaces in which decomposition takes place in the CVD reactor 10 are substrates 30. In reality, and depending on the size and flow conditions within the reactor 10, a relatively small portion of the ligand will react at undesirable surface locations within the reactor. Therefore, this small amount of surface area must be accounted for in the preceding calculation.

The thickness of the thin film, T, deposited on the substrate is therefore equal to the below time-integrated expression:

$$T = \int_o^t R(t)\,dt \tag{35}$$

where the limits of the integral are from the start of the deposition, time=0, to the end of the deposition process, time=t.

In the described reaction equation, tungsten hexafluoride ($WF_6$) and hydrogen carrier gas ($H_2$) combine to form a solid deposit of tungsten wherein hydrogen fluoride (HF) is the exhaust product. As a result of inefficiency (i.e., less than 100% reaction) in the reaction chemistry, it is normal for each of the precursor and carrier gas components to also be a portion of the exhausted products from the reactor. It is the measurement of the reacted and unreacted percentages of the exhausted products which is now a described feature of the present invention.

Assuming the reactor's efficiency to be labeled as E, there are two components to the exhaust stream. First, the unreacted fraction, referred to as (1−E), is directly exhausted and in terms of the input mass flow is calculated as:

$$\text{unreacted fraction} = [(1-E)W] \tag{36}$$

Where W is the measured flow rate of the input precursor (sccm).

The volatile reaction by-products are calculated from the known decomposition reaction (equation 29) and the reactor's measured efficiency, E; previously derived using (equation 28) and a nomograph such as depicted in FIG. 3, or a calculating machine to determine the reacted fraction from the measurables. This calculation is derived from the chemical reaction and the chemical balance of the particular disassociation process, starting from the mass quantity reacted.

$$[EW] \tag{37}$$

It can be shown that:

$$E = \frac{\Delta A + \frac{b}{a}\Delta B}{A + xB} \tag{38}$$

in the context of the generic reaction equation (12) $aA + bB \leftrightharpoons cC + dD$.

The chemical breakdown equations form the basis of the calculation of each of the individual reaction components being exhausted. There may be several reaction components created by the reaction, each of which must be calculated according to its particular molecular weight and mass balance considerations.

We have solid deposit $$\frac{n_1 \Delta d}{a}$$

of species D, and gas phase exhaust, comprising $$\frac{n_1 \Delta c}{a}$$

of species C, $(1-\Delta)n_1$ of species A, and $$n_1\left(x - \frac{b}{a}\Delta\right)$$

of species B.

From the aforementioned discussion, it is clear that x can be inferred from the binary gas analysis of the inlet sample and $\Delta$ (reacted product fraction) from the gas analysis of the exhaust sample.

From the knowledge of mass flow of species A, $n_1$ can be deduced (moles/unit time). Then the composition of the exhaust stream is completely known in terms of its constituents and the respective weights of each. Thus, $$\int_o^t n_1 \, dt\left(\frac{\Delta c}{a} M_C\right) \qquad (39)$$

yields the number of grams of species C exhausted in the time interval t. Similar relations hold for the remaining species in the exhaust stream.

| PARTS LIST FOR FIGS. 1–8 | |
|---|---|
| 10 | system |
| 11 | reactor |
| 12 | housing |
| 14 | cavity or chamber |
| 15 | liquid precursor source |
| 16 | inlet port |
| 17 | liquid injector |
| 18 | outlet port |
| 20 | carrier gas bottle |
| 20A | container |
| 21 | regulating valve |
| 22 | bubble chamber |
| 23 | headspace |
| 24 | mass flow controller |
| 25 | mass flow controller |
| 26 | heater element |
| 27 | mass flow controller |
| 28 | resistance thermometers |
| 29 | supply |
| 30 | substrate |
| 31 | regulator |
| 32 | valve |
| 33 | regulating valve |
| 34 | valve |
| 35 | solenoid leak valve |
| 36 | valve |
| 37 | vaporizer |
| 38 | by-pass line |
| 40 | first acoustic gas composition cell |
| 41 | analyzer |
| 42 | back pressure controller |
| 43 | flow restriction |
| 44 | housing |
| 45 | pressure gauge |
| 46 | acoustic cavity |

-continued

| PARTS LIST FOR FIGS. 1–8 | |
|---|---|
| 47 | exhaust pump |
| 48 | acoustic cavity |
| 50 | second acoustic gas composition cell |
| 51 | Roots pump |
| 52 | acoustic cavity |
| 53 | exhaust line |
| 54 | diaphragm |
| 55 | throttling valve |
| 56 | diaphragm |
| 57 | feedback gauge |
| 58 | O-ring |
| 60 | groove |
| 61 | turbomolecular pump |
| 62 | gas-inlet tube |
| 63 | diaphragm pump |
| 64 | gas inlet |
| 65 | back pressure controller |
| 66 | mounting holes |
| 68 | microphone driving |
| 70 | microphone receiving |
| 74 | gas-outlet tube |
| 76 | gas outlet |
| 77 | platinum RTD |
| 84 | end washers |
| 86 | housing |
| 90 | chamber |

While the present invention has been described according to a preferred embodiment, it will be realized that other modifications and changes can be made within the scope of the appended claims.

For example, one or more infrared spectrometers, or FTIRs (Fourier Transform Infrared Spectrometers), may alternately be used in lieu of acoustic gas composition cells to measure the precursor density at the inlet and outlet to determine the utilization factor. The utilization factor can then be used to determine the growth rate on the substrate in the reactor.

We claim:

1. A method of calculating the composition of gases exhausted from a CVD process reactor, said method comprising the steps of:

measuring the inlet composition of a gas composition entering the reactor using a first acoustic cell disposed in relation to an inlet side of said reactor;

measuring the composition of gas mixture exiting said reactor using a second acoustic cell disposed in relation to an outlet side of said reactor, said second acoustic cell being disposed downstream of at least one vacuum pump disposed between the outlet side of said reactor and said second acoustic cell;

determining the reaction efficiency of the reactor from the measured inlet side and outlet side gas compositions;

determining the unreacted mass fraction of the exhausted gas components;

determining the composition of the reacted gas components; and adding the reacted and unreacted gas components to determine the total exhausted gases.

2. A method as recited in claim 1, wherein the unreacted fraction is calculated from the following relationship:

$$W(1-E)$$

in which:

W=input mass flow rate of precursor; and

E=reaction efficiency for the chemical reaction $aA+aB \rightleftharpoons cC+dD$.

3. An apparatus for determining the reaction efficiency of a CVD reactor, said reactor having a defined cavity for retaining at least one substrate onto which is deposited a solid reaction product from a reacted binary gas mixture (aA+bB⇌cC+dD), said reactor further including an inlet side and an outlet side, said apparatus comprising:

a first acoustic cell for determining the composition of said gas mixture at the inlet side of the reactor;

a second acoustic cell for determining the composition of said gas mixture at the inlet side of the reactor;

pump means disposed between the outlet side of said reactor and said second acoustic cell; and a bypass line extending directly between the first and second acoustic cells;

each said acoustic cell being capable of measuring relative differences in the speed of sound for gases passing therethrough, in which the reacted product is derived from the relation:

$$\left(\frac{\bar{c}_o}{\bar{c}}\right)^2 = \frac{(1-\Delta)M_A + \left(x - \frac{b}{a}\Delta\right)M_B + c\frac{\Delta}{a}M_C}{M_A + xM_B} \cdot$$

$$\left[\frac{1+x}{1+x+\frac{\Delta}{a}(c-b-a)}\right]^2 \left[\frac{\frac{1-\Delta}{\gamma_A} + \frac{x-\frac{b}{a}\Delta}{\gamma_B} + c\frac{\Delta}{\gamma_C}}{(1/\gamma_A + x/\gamma_B)}\right]$$

in which:

$\Delta$=reacted product;

$M_A$, $M_B$, $M_C$=molecular weights of A, B, C;

$\gamma_A$, $\gamma_B$, $\gamma_C$=specific heat ratios of A, B, C;

x=mole fraction of A; and $$\left(\frac{\bar{c}_o}{\bar{c}}\right)$$

is the frequency ratio of the gas mixture between a reacted mode and a bypass mode.

4. Apparatus as recited in claim 3, including at least one mass flow meter for controlling the mole fraction of A entering said inlet side.

5. Apparatus as recited in claim 3, wherein said pump means includes a turbomolecular pump and a diaphragm pump disposed between the outlet of said reactor and said second acoustic cell.

6. Apparatus as recited in claim 3, wherein said pump means includes a multi-stage piston pump.

\* \* \* \* \*